(12) United States Patent
Sabherwal et al.

(10) Patent No.: US 12,377,075 B2
(45) Date of Patent: *Aug. 5, 2025

(54) DEVICE FOR INTERNAL AND EXTERNAL NASAL APPLICATION

(71) Applicant: HALEON CH SARL, Prangins (CH)

(72) Inventors: Amit Sabherwal, Gurgaon (IN); Thierry Athanase, Prangins (CH); Sriman Banerjee, Warren, NJ (US)

(73) Assignee: HALEON CH SARL, Prangins (CH)

( * ) Notice: Subject to any disclaimer, the term of this patent is extended or adjusted under 35 U.S.C. 154(b) by 632 days.

This patent is subject to a terminal disclaimer.

(21) Appl. No.: 17/776,048

(22) PCT Filed: Nov. 12, 2020

(86) PCT No.: PCT/EP2020/081908
§ 371 (c)(1),
(2) Date: May 11, 2022

(87) PCT Pub. No.: WO2021/094451
PCT Pub. Date: May 20, 2021

(65) Prior Publication Data
US 2022/0387389 A1 Dec. 8, 2022

Related U.S. Application Data

(63) Continuation of application No. 15/930,847, filed on May 13, 2020.

(30) Foreign Application Priority Data

Nov. 14, 2019 (EP) ..................... 19209288

(51) Int. Cl.
| | | |
|---|---|---|
| A61K 31/4164 | (2006.01) | |
| A61K 9/00 | (2006.01) | |
| A61K 31/045 | (2006.01) | |
| A61K 31/23 | (2006.01) | |
| A61K 31/35 | (2006.01) | |
| A61K 31/569 | (2006.01) | |
| A61K 36/185 | (2006.01) | |
| A61K 36/22 | (2006.01) | |
| A61K 36/47 | (2006.01) | |
| A61K 36/54 | (2006.01) | |
| A61K 36/758 | (2006.01) | |
| A61K 36/899 | (2006.01) | |
| A61P 11/02 | (2006.01) | |
| A61P 17/16 | (2006.01) | |

(52) U.S. Cl.
CPC ........ *A61K 31/4164* (2013.01); *A61K 9/0014* (2013.01); *A61K 9/0043* (2013.01); *A61K 31/045* (2013.01); *A61K 31/23* (2013.01); *A61K 31/35* (2013.01); *A61K 31/569* (2013.01); *A61K 36/185* (2013.01); *A61K 36/22* (2013.01); *A61K 36/47* (2013.01); *A61K 36/54* (2013.01); *A61K 36/758* (2013.01); *A61K 36/899* (2013.01); *A61P 11/02* (2018.01); *A61P 17/16* (2018.01)

(58) Field of Classification Search
None
See application file for complete search history.

(56) References Cited

U.S. PATENT DOCUMENTS

2018/0044077 A1 2/2018 Teller et al.

FOREIGN PATENT DOCUMENTS

| CN | 2227615 Y | 5/1996 | |
|---|---|---|---|
| CN | 101756964 A | 6/2010 | |
| CN | 106137801 A | 11/2016 | |
| JP | 2006008516 A * | 1/2006 | |
| WO | 2007113551 A1 | 10/2007 | |
| WO | WO-2019006173 A1 * | 1/2019 | ........... A61K 31/335 |

OTHER PUBLICATIONS

English language translation of JP 2006 008516 A, Publ. Jan. 12, 2006. (Year: 2006).*

* cited by examiner

*Primary Examiner* — Dominic Lazaro
(74) *Attorney, Agent, or Firm* — E. Eric Mills; Nicholas P. Stadnyk; Maynard Nexsen PC

(57) ABSTRACT

A combination product comprising a dispensing head (10, 10') mounted on a top of a container (20, 20') containing a formulation for nasal administration, and a solidified skin-care balm (50) for application around the nose contained in a balm holder element (30, 30") located on a bottom (24) of the container (20).

18 Claims, 4 Drawing Sheets

Fig. 1
Fig. 2
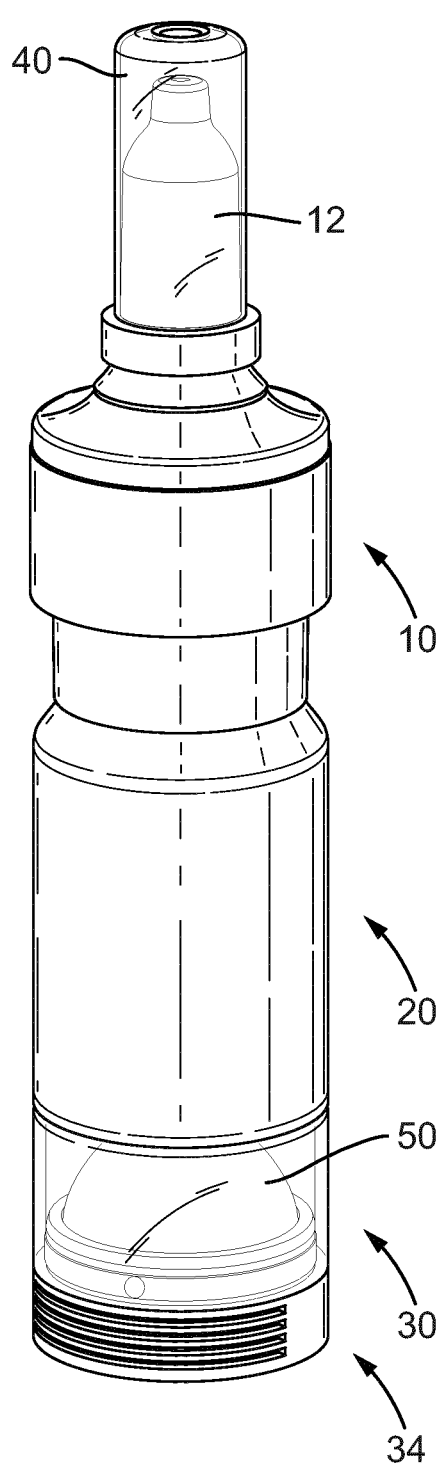
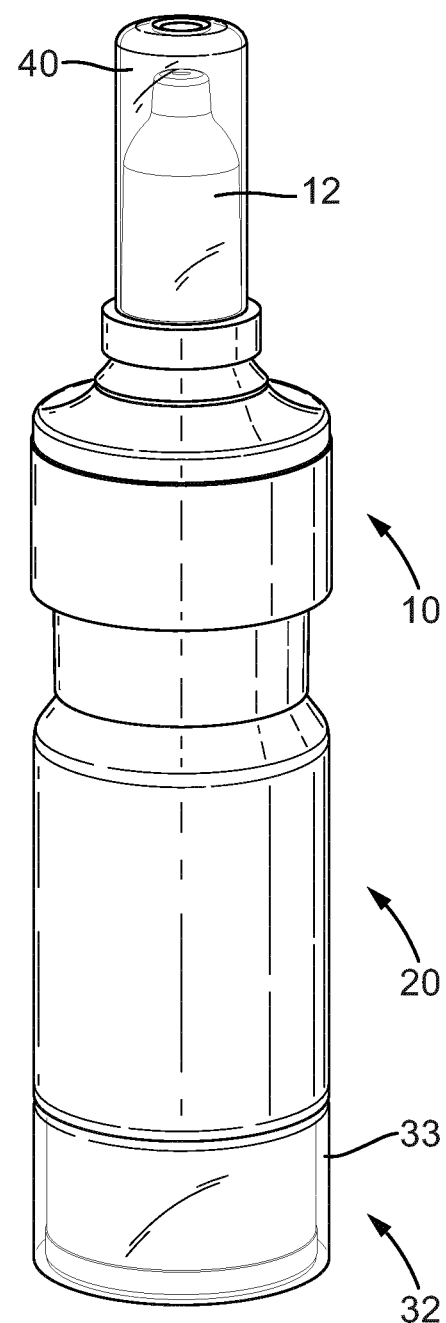

DEVICE FOR INTERNAL AND EXTERNAL NASAL APPLICATION

CROSS-REFERENCE TO RELATED APPLICATIONS

This application is a 371 of International Application No. PCT/EP2020/081908, filed 12 Nov. 2020, which claims the benefit of U.S. Ser. No.: 15/930,847, filed 13 May 2020 and European Patent 19209288.0 filed 14 Nov. 2019.

FIELD OF THE DISCLOSURE

This disclosure relates to a novel combination product. The combination product comprises a nasal spray product comprising a dispensing head mounted on a top of a container containing a liquid formulation for nasal administration.

BACKGROUND OF THE DISCLOSURE

Intranasal administration of a liquid formulation, for example a drug formulation or a medicinal product formulation, frequently employs a primary packaging for such formulation that comprises a container and a dispensing mechanism with a nozzle that is suitable to be introduced to a user's nostril and from which such liquid formulation is dispensed into the nostril. In particular for liquid formulations containing an active ingredient, where it is important that the desired dose of the ingredient is administered, metered dose spray pumps are commonly used as a dispensing mechanism.

Metered dose spray pumps are for example known from EP1768789B3, EP1954403B1, or WO2017191205A1.

The nasal administration of saline solutions which may in addition contain active ingredients is a widely used method of treatment. Active ingredients which come into consideration are, for example, vasoconstrictors, such as xylometazoline, or antiallergic agents, such as cromoglycic acid or H1 receptor antagonists, e.g. dimethindene maleate. Another group of possible active ingredients is e.g. corticosteroids, such as beclomethasone or fluticasone.

The indications in which a certain nasally administered drug is to be applied are known in the art. For example, vasoconstrictors are e.g. used as nasal decongestants for alleviating the typical symptoms of common cold or flu, like running nose, obstructed nose etc., or in rhinitis or sinusitis. Antiallergic agents and corticosteroids are e.g. used in allergic conditions, e.g. hay fever, or in asthmatic or inflammatory conditions.

Patients who suffer from any of these conditions do in general frequently use tissues to blow their nose or to clean their nose. This frequently leads to skin irritation and redness around the nose, which generally occurs soon after the onset of the symptoms which are treated by the intranasal administration of a liquid formulation. This irritation or redness can in certain circumstances and depending on the active ingredients even be exacerbated by the liquid formulation which has been administered, but does not stay in the nostrils.

Today, patients and consumers either leave this skin irritation untreated, or treat it with skin creams or balms sold separately for different purposes, and/or conceal it with make-up or other cosmetic products. However, existing cream or balm formulations in the market are not necessarily suitable for treating the irritation and redness around the nose, and the use of concealer or make-up does not treat the condition, and might even worsen it. Furthermore, using a nasal spray and a separate product such as a cream or balm is not convenient, especially when both products need to be used several times per day, and users are not staying at home but travel or commute to their workplace, school or other locations.

There is thus a need for a solution allowing users to conveniently treat the skin irritation and redness around the nose occurring frequently together with nasal congestion or a running nose.

SUMMARY OF THE DISCLOSURE

This disclosure therefore provides a novel combination product comprising a dispensing head mounted on a top of a container containing a formulation for nasal administration, and a solidified skin-care balm for application around the nose, contained in a balm holder element located on a bottom of the container.

According to a preferred embodiment, the dispensing head is a metered dose spray pump.

According to a preferred embodiment, the balm holder element comprises a base element on which the balm is mounted, and a balm cover with a cylindrical portion surrounding the balm, and a cover portion.

According to a preferred embodiment, the cylindrical portion of the balm cover is aligned with a cylindrical wall of the container containing the formulation.

According to another preferred embodiment, the balm cover is attached to the bottom of the container.

According to yet another preferred embodiment, the balm cover is glued to the bottom of the container.

According to a preferred embodiment, the cover portion is dome-shaped and matches a recess in the bottom of the container containing the formulation.

According to another preferred embodiment, the balm cover is clipped or snap-fitted to the bottom of the container.

According to another preferred embodiment, the base element of the balm holder element is attached to the bottom of the container.

According to a preferred embodiment, the liquid formulation comprises a saline solution and/or an active ingredient selected from the group of vasoconstrictors, antiallergic agents and corticosteroids.

According to another preferred embodiment, the active ingredient is xylometazoline or a pharmaceutically acceptable salt thereof.

According to a preferred embodiment, the balm comprises an active ingredient having skin soothing properties, in particular selected from the group comprising ectoin, dexpanthenol, aloe vera, calendula, bisabolol and niacinamide.

According to a preferred embodiment, the solidified balm has substantially a hemispherical shape.

According to a preferred embodiment, the balm comprises one or several skin conditioning agents.

According to another preferred embodiment, the balm comprises an active ingredient that is a botanical extract.

This disclosure further provides a balm holder element comprising: a base element on which a balm is mounted, a balm cover with a cylindrical portion surrounding the balm, and a cover portion, wherein the balm holder element is attachable to a nasal spray dispenser.

This disclosure further provides a method for treating nasal discomfort whereby a cooling and soothing effect is provided to a perinasal skin area, comprising use of a combination product of the present disclosure by application of the balm to the perinasal skin area and administration of the formulation for nasal administration into a nostril.

This disclosure further provides a method for treating runny nose whereby irritated skin is soothed, comprising use of a combination product of the present disclosure by application of the balm to an irritated perinasal skin area and administration of the formulation for nasal administration into a nostril.

There is provided a combination product comprising a dispensing head mounted on a top of a container containing a liquid formulation for nasal administration, and a solidified skin-care balm for application around the nose contained in a balm holder element attached to a bottom of the container. In a preferred embodiment, the dispensing head is a metered dose spray pump. In a preferred embodiment, the balm holder element comprises a base element on which the balm is mounted, and a balm cover with a cylindrical portion surrounding the balm, and a cover portion. In another preferred embodiment, the cylindrical portion of the balm cover is aligned with a cylindrical wall of the container containing the liquid formulation. In yet another preferred embodiment, the balm cover is attached to the bottom of the container. Preferably in embodiments with the balm cover attached to the bottom of the container, the balm cover is glued to the bottom of the container. In those embodiments it is further preferred that the cover portion is dome-shaped and matches a recess in the bottom of the container containing the liquid formulation. Alternatively, the balm cover may be clipped or snap-fitted to the bottom of the container.

There is also provided a combination product wherein the base element is attached to the bottom of the container.

In a preferred embodiment, the liquid formulation contains a saline solution and an active ingredient selected from the group of vasoconstrictors, antiallergic agents and corticosteroids. In a more preferred embodiment the active ingredient is xylometazoline or a pharmaceutically acceptable salt thereof.

In a preferred embodiment, the balm comprises an active ingredient having skin soothing properties, in particular selected from the group comprising ectoin, dexpanthenol, aloe vera, calendula, bisabolol and niacinamide.

In another preferred embodiment, the solidified balm has substantially a hemispherical shape. In yet another preferred embodiment, the balm comprises one or several skin conditioning agents.

The balm holder element is located on a bottom of the container. Thereby, the dispensing head which is mounted on a top of a container can be used without hindrance by the balm holder element. Furthermore it is beneficial for the balance of the combination product, as it results in a lower center of gravity which is beneficial for a stable stand on an even surface.

The balm holder element may be formed in one piece with the container on the bottom of the container. For example, the container and either the balm cover, or the base element of the balm holder element, may be moulded from plastic material in the same mould and moulding step. Preferably, a part of the bottom of the container acts as the cover portion or the base element.

Alternatively, the balm holder element may also be manufactured individually from the container. The balm holder element, for example the base element or the balm cover, may then be attached to the bottom of the container in a separate manufacturing step. This provides the advantage that conventional containers for nasal formulations may be used for the combination product of the present disclosure. These conventional containers may be equipped with the balm holder element before or after filling with the formulation for nasal administration and closing of the container. If the container and the balm holder are manufactured individually, they may be made from distinct materials.

Preferably, the balm holder element is made from polypropylene (PP). Preferably, both the base element and the balm cover of the balm holder element are made from polypropylene (PP). It should be noted that the term "attached to a bottom" should not be understood as limited to an attachment of the balm cover or the base element to a bottom surface of the container, but that the balm holder element can also be attached to a bottom part of the cylindrical wall of the container. Preferably, the balm holder element is located on a bottom surface of the container.

Thereby the combination product can stand upright on an even surface on the balm holder element.

Typically, and as known in the art, the container containing the liquid formulation is made from high density polyethylene (HDPE). Alternatively, the container may be made from polypropylene (PP). In yet another alternative, the nasal spray dispenser and the container may be made from glass.

According to a preferred embodiment, the dispensing head is a metered dose spray pump. Metered dose spray pumps are primarily used for administration of liquid formulations for nasal administration comprising active ingredients. These active ingredients are used for the treatment of conditions that frequently cause irritation of the perinasal skin like runny nose. It is therefore especially advantageous to equip products with this kind of dispensing head with a balm holder element to provide a combination product of the present disclosure.

According to a preferred embodiment, the balm holder element comprises a base element on which the balm is mounted, and a balm cover with a cylindrical portion surrounding the balm, and a cover portion. The balm may be moulded into or onto the base element. Alternatively, the balm may be moulded in a mould and subsequently attached to, such as pressed onto, the base element. The balm cover is detachably attached to the base element. For example, the balm cover may be screwed or press fitted onto the base element to close the balm holder element. Preferably, the base element and the balm cover are connectable by a thread. To close the balm holder element, the balm cover is attached to the base element. The balm cover covers the balm when the balm holder element is closed.

Preferably, the part of the balm holder element that is adjunct to the container of the container of the nasal spray product corresponds to its outline. Thus, when the container has an ellipsoid or ovoid outline, the part of the balm holder element located adjunct to the container has a corresponding elliptic or oval cylinder portion. For example, when the balm cover is attached to the bottom of the container, and the container has a circular outline, the balm cover has a corresponding circular cylindrical portion. Preferably, the container has a circular outline and the balm cover has a corresponding circular outline. In those embodiments, it is especially preferred that the base element also has a corresponding circular outline and the base element, and the balm cover are connectable by a thread.

Preferably, the cylindrical portion of the balm cover is aligned with a cylindrical wall of the container containing the liquid formulation.

According to one preferred embodiment, the balm cover is attached to the bottom of the container. The user can then take off the base element with the balm and apply the balm without having to handle the container and the dispensing head during balm application.

Preferably, the balm cover is glued to the bottom of the container. A suitable glue for attaching the balm cover to the container, in particular when the balm cover is made from PP and the container out of HDPE, is cyano-acrylate glue which is used together with a primer. No heating is necessary to create the bond, and such a glue is thus particularly suitable to be used with a pre-filled container, where the application of heat in an assembly process could compromise the stability of the liquid formulation contained in the container.

Preferably, the cover portion of the balm cover is dome-shaped and matches a recess in the bottom of the container containing the liquid formulation. This improves the bond between the balm cover and the container.

As an alternative to the glued connection the balm cover is clipped or snap-fitted to the bottom of the container. Depending on the design of the connection, this can also allow for an assembly or disassembly by the consumer.

In another embodiment, the balm element is mounted on the container with friction fit. In one embodiment, the balm cover of the balm element is attached to the container by friction fit. In another embodiment, the base element of the balm element is attached to the container with friction fit. The friction fit may be in a strength such that the balm element can be detached from and attached to the container by a user. Alternatively, the friction fit may be in a strength such that the balm element may not be detached from the container manually after initial assembly. Suitably, the part of the balm holder element that is mounted on the container with friction fit, that is either the base element or the balm cover, has a friction fit portion into which the container can be introduced to provide the friction fit. For example, if the balm cover is attached to the container by friction fit, the cylindrical portion of the balm cover may be in a length such that it projects beyond the bottom surface of the container when the container is attached to the balm cover. The friction fit is then provided between the inner surface of the cylindrical portion and the outer surface of the container, where the two components are in contact.

According to an alternative embodiment, instead of the balm cover, the base element is attached to the bottom of the container. Similarly to what was described above, the base element can be glued, clipped, friction fitted or snap-fitted to the container, or attached in any other suitable way, either removable or non-removable for the consumer.

The formulation for nasal administration may be in a powdered (dry) form or may be in a liquid form, such as a solution or a liquid suspension.

Preferably, the formulation for nasal administration is a liquid formulation. Upon nasal administration of liquid formulations it often occurs that the formulation does not remain in the nose, but flows out of the nostrils. This requires wiping, which may cause skin irritation. Also, the discharge of the liquid formulation may further irritate the perinasal skin or have a burning sensation on the irritated perinasal skin. This is prevented by the use of the provided combination product. The balm forms an occlusive film that prevents interaction between the liquid formulation and the perinasal skin. The balm also forms an occlusive film that prevents interaction between physiological nasal discharge and the perinasal skin.

According to a preferred embodiment, the liquid formulation contains a saline solution and/or an active ingredient selected from the group of vasoconstrictors, antiallergic agents and corticosteroids.

Active substances suitable for nasal administration are e.g. vasoconstrictors, e.g. xylometazoline, e.g. xylometazoline hydrochloride; indanazoline, metizoline; naphazoline, e.g. naphazoline hydrochloride; fenoxazoline, e. g. fenoxazoline hydrochloride; oxymetazoline, e.g. oxymetazoline hydrochloride; tetrahydrozoline, tramazoline, tymazoline; phenylephrine, e.g. phenylephrine hydrochloride; ephedrine, e.g. d-pseudoephedrine hydrochloride; or epinephrine; or antiallergic agents, such as (1) cromoglycic acid (=cromolyn) or a nasally acceptable salt thereof, e.g. the disodium salt (=disodium cromoglycate), or (2) H1 receptor antagonists, e.g. dimethindene or a nasally acceptable salt thereof, e.g. dimethindene maleate; acrivastine, brompheniramine, chlorpheniramine, dexchlorpheniramine, triprolidine, bromodiphenhydramine, clemastine, phenyltoloxamine, piprinhydrinate, pyrilamine, tripelennamine, cetirizine, hydroxyzine, methdilazine, promethazine, trimeprazine, azatadine, cyproheptadine, loratadine, astemizole, diphenhydramine, levocabastine or terfenadine. Examples for corticosteroids are e.g. beclomethasone, e.g. beclomethasone dipropionate, or fluticasone, e.g. fluticasone propionate. Mixtures of more than one active substance come also into consideration, e.g. a combination of a vasoconstrictor and an antiallergic agent, such as xylometazoline plus cromoglycic acid or phenylephrine plus dimethindene, or a combination of a vasoconstrictor and a corticosteroid, such as xylometazoline plus beclomethasone.

Preferably, the active ingredient is xylometazoline or a pharmaceutically acceptable salt thereof. Xylometazoline is widely used in particular for treating symptoms of common cold and flu, where the skin irritation and redness issues arise frequently.

In another embodiment, the active ingredient is oxymetazoline or a pharmaceutically acceptable salt thereof.

In yet another embodiment, the liquid formulation is a hypertonic saline solution.

In still another embodiment, the liquid formulation is an isotonic saline solution.

Preferably, the liquid formulation further comprises a moisturizing agent, in particular selected from the group comprising dexpanthenol, sorbitol and hydroxypropylmethylcellulose.

According to a preferred embodiment, the balm comprises an active ingredient having skin soothing properties, in particular selected from the group comprising ectoin, dexpanthenol, aloe vera, calendula, bisabolol and niacinamide.

In another embodiment, the balm comprises an active ingredient that is a botanical extract. A botanical extract may be an extract from any part of a plant, e.g. an herbal extract. Botanical extracts are widely accepted by consumers, can be sourced environmentally friendly and do not need to be chemically synthesized. Botanical extracts from edible plants are preferred as they are non-toxic and can be used in the perinasal and perioral area, such as the upper lip region, without limitation. The ingredients of the extracts can be controlled such that desired and effective ingredients are enriched, and undesirable ingredients are reduced or eliminated.

In one embodiment, the botanical extract is *Zanthoxylum bungeanum* fruit husk extract. This extract is rich in lipophilic alkylamides such as hydroxy-alpha-sanshools and hydroxy-beta-sanshools. These agents act as agonists on receptors of sensory neurons, such as the transient receptor potential cation channel subfamily V member 1 TRPV1 (also known as capsaicin receptor, or vanilloid receptor) and the transient receptor potential cation channel subfamily A member 1, 1TRPA1. The interaction of the ingredients of the extract with the somatosensory neurons in the skin provides a soothing, numbing and anti-itching effect that is especially suitable for the balm of the combination product. It provides a mild tingling effect and gives an immediate relief. Its soothing or paresthesial effect reliefs the discomfort of the user, reduces the sensitivity of the skin and reduces the body's response to irritation such as runny nose, tearing and skin reddening. *Zanthoxylum bungeanum* fruit husk extract is not irritating to the skin and does not cause sensitisation. Additionally it has a pleasant smell that can mask any odour that might be inherent to further components of the balm. The balm can therefore be formulated without perfume, which is preferred as perfumes can cause skin irritation or burning sensation, especially when used on damaged skin. Preferably, the *Zanthoxylum bungeanum* fruit husk extract is obtained by a mild, solvent free extraction method such as $CO_2$ extraction. This provides the advantage of a high yield of the lipophilic alkylamides with no residual organic solvents.

The *Zanthoxylum bungeanum* fruit husk extract may typically have a content of total alkylamides of 4% to 7% by weight and may be used in the formulation of the balm in an amount from 0.05% to 1.0% by weight.

In an alternative embodiment, the botanical extract comprises Aloe Barbadensis leaf extract. Aloe Barbadensis leaf extract has a moisturizing effect that is beneficial for roughened and cracked skin and helps to soothe irritated skin. Typically, the Aloe Barbadensis leaf extract is used in the formulation of the balm in an amount of 0.05% to 1% by weight.

Alternatively or in addition to such an active ingredient, the balm can contain skin conditioning or mistering agents. Alternatively or in addition to these ingredients, the balm can contain one or more emollients.

Preferably, the balm is a non-aqueous formulation. This reduces the risk of contamination of the balm upon contact with the skin and allows to formulate a preservative-free formulation. This is beneficial as the balm may be used on irritated skin with an impaired barrier-function.

Furthermore, a non-aqueous formulation forms a waterproof film or barrier layer on the irritated perinasal skin that has an occlusive, thus hydrating effect and protects the skin from nasal discharge and wiping with tissues that typically exacerbate irritation of the skin. Such an occlusive film is furthermore preferred as it may serve as a substitute for a disrupted natural skin barrier, may aid to restore the natural skin barrier which prevents the skin from being damaged further, and may reduce trans epidermal water loss.

The balm formulation preferably comprises a blend of two or more waxes in an amount of 15%-45% by weight of the composition. The use of a blend of two or more waxes lowers the melting point which eases application to the skin. The use of a blend also reduces the tendency of the waxes to form large crystals, which would make the balm grainy or brittle.

The terms wax and waxes, as used herein, comprise waxes and pseudo-waxes. Numerous waxes or pseudo-waxes of animal, plant or petroleum origin known in the art are suitable for the formulation of the balm. Pseudo-waxes are excipients that have physical properties similar to those of waxes but are not waxes in the chemical sense, i.e. esters of fatty acids with fatty alcohols. They may be mixtures of hydrocarbons and/or fatty acids and/or fatty alcohols and/or fatty acid esters and/or hydrogenated or unhydrogenated oils (triglycerides). Examples for hydrocarbons are petrolatum and paraffin.

In one embodiment, the balm comprises a blend of petrolatum and paraffin. Petrolatum and paraffin are non-irritating, well-established and abundant hydrocarbons.

Preferably the balm is a solidified skin-care balm. Solidified, in the present disclosure, is to be understood as not liquid at 20° C. More preferred is that the balm is not liquid at 30° C., and most preferred is that the balm is not liquid at 40° C.

Preferably, the melting temperature of the balm is in the range from 60° C. to 75° C. Melting temperature is determined according to the method monographed in the European Pharmacopoeia, Melting point open capillary method, Ph. Eur. Edition 10, method 2.2.15. This melting temperatures reduces the tendency of sweating or creaming of ingredients. It also provides firm adhesion of the balm to the balm base and structural integrity of the balm shape, even in warm climates. At the same time, the balm is still soft enough for easy application to the skin and a convenient spread. Preferably, this melting temperature is achieved by combining a first wax having a melting point of 70° C.-90° C. and a second wax having a melting point of 30° C.-60° C.

Preferably, the first wax is rice bran wax. Rice bran wax gives the balm formulation a matt finish and reduces shine and greasiness when applied to the skin.

Preferably, the balm comprises 15%-45% (w/w) of a blend of two or more waxes, and 45%-70% (w/w) of emollients. The emollients hydrate the roughened skin of the perinasal area and soothe irritation. Furthermore, emollients reduce the hardness of the balm and lower the crystallisation tendency of the waxes, which makes spreading gentler and ensures the texture of the balm remains stable over time.

Preferably, the emollients comprise powdered hydrogenated castor oil. The powdered form of the hydrogenated castor oil reduces shine and greasiness of the balm when applied to the skin. Examples of other suitable emollients are botanical butters such as *Butyrospermum Parkii* (Shea) Butter and *Theobroma Cacao* (Cocoa) Seed Butter, oils such as castor oil and avocado oil, octyldodecanol, caprylic/capric triglyceride, behenyl alcohol, isopropyl lanolate, isopropyl myristate, isocetyl stearate and myristyl myristate.

Emollients comprising unsaturated fatty acids are preferred, for example shea butter and/or avocado oil. Avocado oil is especially preferred as it has a specific composition comprising free fatty acids that provides an excellent compatibility with the natural hydrolipidic film on the skin. The balm may optionally comprise further excipients used in the art such as antioxidants, wetting agents, matting agents, rheology additives, hydrating agents and cooling agents.

Preferably, the solidified balm has substantially a hemispherical shape, thus allowing for easy application.

The balm may be applied to damaged, cracked, roughened, dry and irritated skin. It is especially beneficial for application in the perinasal area, i.e. the skin around the nose and the nostrils and the upper lip region. This area suffers primarily from wiping and nose blowing, nasal discharge, leakage of nasal formulation from the nose and other effects of nasal symptoms. It may also be beneficial for application to the perioral area and the lips. The perioral area and the lips also suffer from the effects of nasal symptoms, such as leakage of nasal formulation or frequent licking. According to a preferred embodiment, the balm is applied to the skin around the nose. In another preferred embodiment, the balm is applied to the skin around the nostrils. The balm may be applied concomitantly with the product for nasal administration. Alternatively, the balm may be applied individually, when needed. For example, the balm may be applied after each cleaning of the nose or multiple times daily.

BRIEF DESCRIPTION OF THE DRAWINGS

FIG. 1 shows a perspective view of a combination product according to a first embodiment FIG. 2 shows a perspective view of the combination product of FIG. 1, with a base element of a balm holder element and a balm being taken off

DETAILED DESCRIPTION OF PREFERRED EMBODIMENTS

The invention will now be described by way of example only with reference to the accompanying figures.

Figure 7:
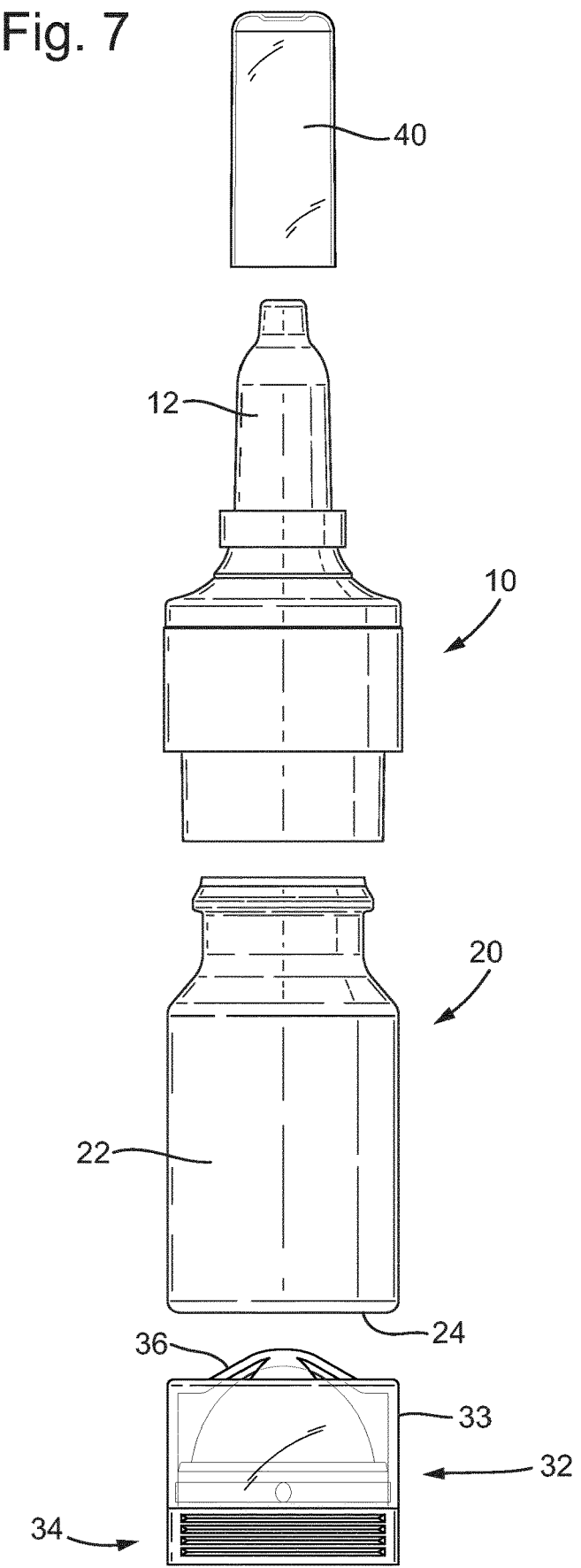
FIG. 7 shows an exploded view of the combination product of FIG. 1

FIGS. 1 and 7 show a combination product which comprises a conventional nasal spray device comprising a HDPE container 20 containing a liquid formulation for nasal administration, and a dispensing head 10, here a metered dose spray pump, with a nozzle 12 to be introduced into a nostril, covered by a cap 40, as well as a balm holder element 30 containing a solidified skin-care balm 50. The balm holder element 30 comprises a balm cover 32 and a base element 34 holding the balm 50.

Figure 3:
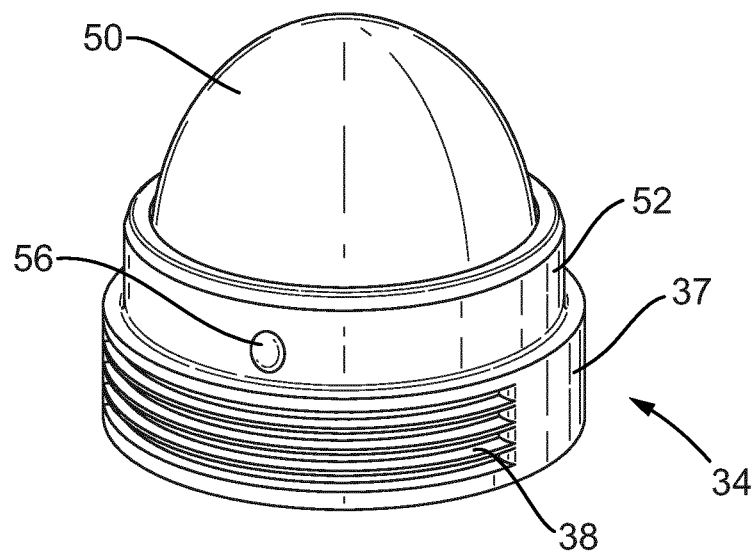
FIG. 3 shows a base element and a balm according to the first embodiment

FIG. 2 shows the same combination product, where the base element 34 carrying the balm 50 has been taken off. FIG. 3 shows the base element 34 of the embodiment of FIG. 1, together with the balm, separately and ready to be used. The base element 34 is moulded in one piece and has a circular base plate 37, with a circumferential rim 52 on that base plate 37 surrounding the solidified balm 50. Protrusions protruding inwardly from the circumferential rim 52 can be used to hold the solidified balm 50 in place, once it has been pressed on the base plate 37 and on same protrusions. Alternatively, the base element 34 and the balm 50 may be assembled upon moulding of the balm whereby a molten balm formulation solidifies on the base element 34. In the first embodiment shown in FIGS. 1 and 3, the base element 34 is provided with circumferential ribs 38 running along parts of the circumference of the base plate 37 and making it easier to grip the base plate 37 and thus the base element 34 with the balm 50.

The balm 50 has a substantially hemispherical shape, and an example for a formulation is given in Table 1.

The balm cover 32 consists of a cylindrical portion 33 surrounding the balm 50, and a cover portion 36 which has a domed shape, as it can be seen in FIG. 7. The cover portion 36 with its domed shape matches a corresponding recess in the bottom 24 of the container 20, and it is glued on the bottom 24 using a primer and cyano-acrylate glue. Both the balm cover 32 and the base element 34 are made of Polypropylene (PP).

On the outer surface of the rim 52, several protrusions 56 are foreseen, which make a snap-fit connection with the cylindrical portion 33 of the balm cover 32 and help to keep the base element 34 connected to the balm cover 32, and thus to the container 20.

Figure 4:
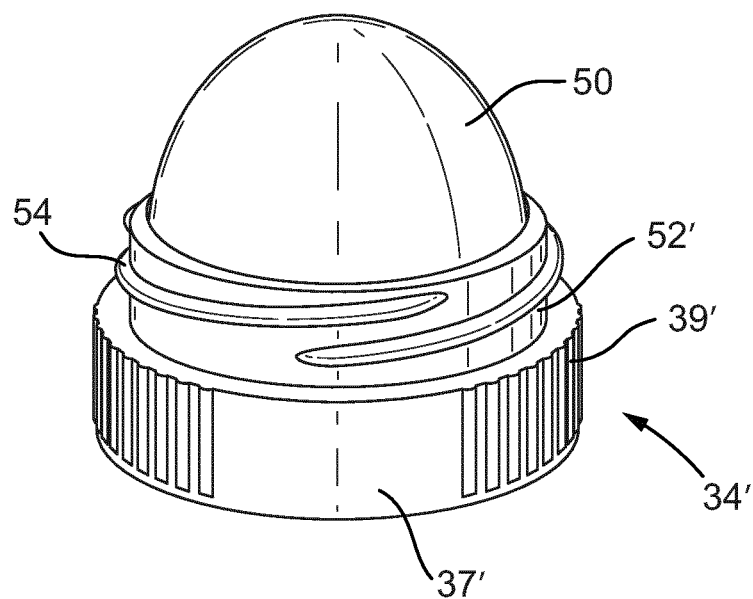
FIG. 4 shows a base element and a balm according to a second embodiment

FIG. 4 shows an alternative embodiment of a base element 34' carrying the same solidified balm 50. While the overall shape of the base plate 37' and the circumferential rim 52' are the same as for the first embodiment shown in FIGS. 1 and 3, the rim 52' is in this embodiment provided with a thread 54 which matches a thread at the inner circumference of the cylindrical portion of the balm cover (not shown in the figures). Furthermore, in the embodiment shown in FIG. 4, the base element 34' also has ribs 39 on the outer circumference of the circular base plate 37', but these are perpendicular to the circumference of the base plate 37'.

Figure 5:
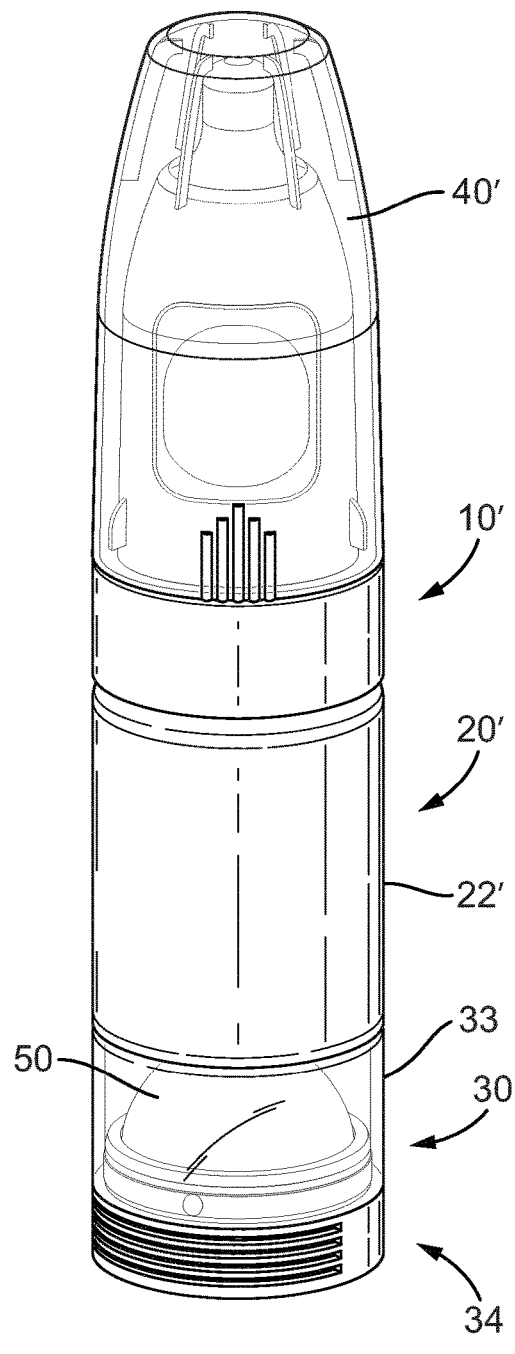
FIG. 5 shows a perspective view of a combination product according to a third embodiment

FIG. 5 shows an embodiment of a combination product according to the disclosure, differing from the embodiment shown in FIG. 1 in the choice of the container 20' and the metered dose spray pump 10'. Here, a laterally actuated pump 10' as for example described in WO2017191205A1 is used. The balm holder element 30 is the same as in the embodiment shown in FIGS. 1 and 3.

Figure 6:
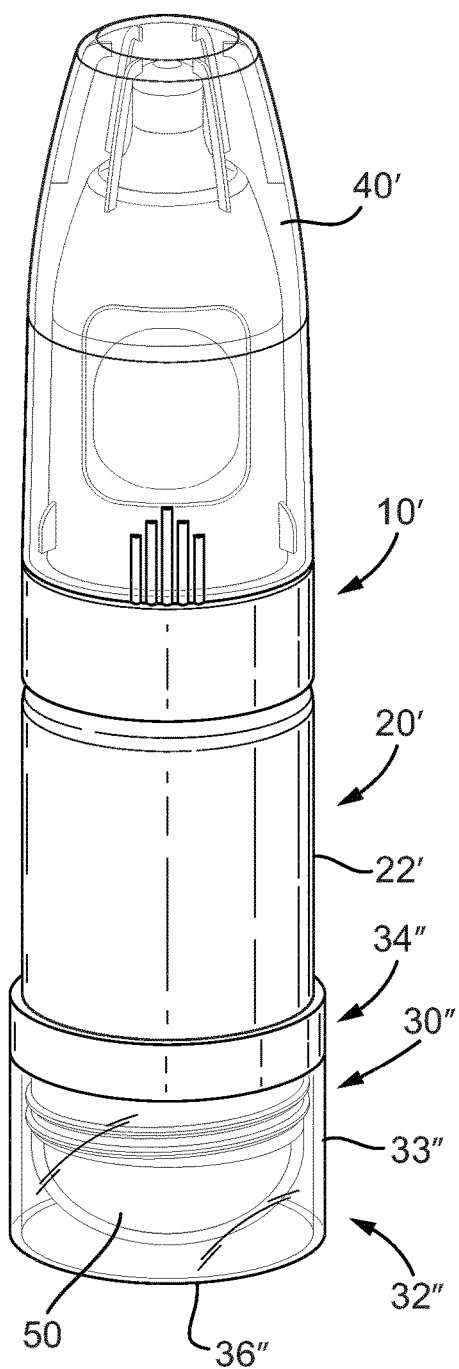
FIG. 6 shows a perspective view of a combination product according to a further embodiment, with a base element attached to a bottom of a container.

FIG. 6 shows another embodiment of a combination product according to the disclosure, using the same container 20' and the same laterally actuated metered dose spray pump 10', but a different balm holder element 30". As it can be seen when comparing FIGS. 5 and 6, the orientation of the balm holder element 30" is inverted in the embodiment of FIG. 6, with the base element 34" being attached to the bottom of the container 20', and the balm cover 32" being removable. In this embodiment, the base element 34" is not glued on a base surface at the bottom of the container, but it comprises a cylindrical portion extending around the lowest part of the cylindrical wall 22' of the container 20', and can either be glued thereto, or fixed in another way, e.g. via a snap-fit or clip connection. The cover portion 36" of the balm cover 32" is flat, so that the combination product can stand on it.

Example 1

An example for a balm formulation is given below in Table 1.

TABLE 1

Example of a balm formulation

| INCI name of component | % of component in the final formulation | Function of the component |
| --- | --- | --- |
| OCTYLDODECANOL | 17.00 | EMOLLIENT |
| CAPRYLIC/CAPRIC TRIGLYCERIDE | 14.70 | SKIN CONDITIONING |
| RICINUS COMMUNIS SEED OIL | 14.30 | SKIN CONDITIONING |
| ORYZA SATIVA CERA | 14.00 | SKIN CONDITIONING SKIN PROTECTING SMOOTHING |
| RHUS VERNICIFLUA PEEL CERA/RHUS SUCCEDANEA FRUIT CERA | 13.40 | EMOLLIENT STABILISING/ BINDING EMOLLIENT |
| THEOBROMA CACAO SEED BUTTER | 7.00 | EMOLLIENT SKIN CONDITIONING |
| PERSEA GRATISSIMA OIL | 5.00 | SKIN CONDITIONING |
| CETEARYL ALCOHOL | 3.00 | EMOLLIENT EMULSIFYING EMULSION |

TABLE 1-continued

Example of a balm formulation

| INCI name of component | % of component in the final formulation | Function of the component |
|---|---|---|
| MYRISTYL MYRISTATE | 3.00 | STABILISING EMOLLIENT SKIN CONDITIONING |
| POLYGLYCERYL-3 DIISOSTEARATE | 2.50 | EMULSIFYING |
| CETYL ESTERS | 2.00 | EMOLLIENT SKIN CONDITIONING |
| *BUTYROSPERMUM PARKII* BUTTER | 2.00 | SKIN CONDITIONING |
| OLEYL ALCOHOL | 0.48 | EMOLLIENT MASKING |
| *ZANTHOXYLUM BUNGEANUM* FRUIT EXTRACT | 0.12 | SKIN CONDITIONING |
| TOCOPHERYL ACETATE | 0.50 | ANTIOXIDANT |
| MENTHYL ETHYLAMIDO OXALATE | 0.50 | SKIN CONDITIONING |
| Eucalyptol Nat | 0.2 | PERFUMING SKIN CONDITIONING |
| MENTHOL | 0.20 | REFRESHING SOOTHING |
| BHT | 0.10 | ANTIOXIDANT |

The names of the raw materials are given using the International Nomenclature of Cosmetic Ingredients (INCI). The % are indicated by weight.

The balm may be prepared by a conventional method. For the example, it was prepared by melting of the solid components in a water bath at a temperature sufficiently high to melt all ingredients, about 60° C.-70° C. Subsequently, the liquid ingredients were added, and the mixture was stirred to form a bulk. Any volatile ingredients were added after letting the bulk cool under stirring, but whilst the bulk was still fluid. The fluid bulk was poured into a stainless steel mould with an array of recesses of hemispheric shape. Excess bulk was scraped off. The mould filled with the bulk was let cool down at 5° C. for 20 minutes. The solidified balm hemispheres were removed from the mould by turning it upside down and placing it on a hard surface. To produce the combination product, the balm was pressed on the base element (34, 34') and the base element was assembled with the remaining parts of the balm holder element (30, 30") and the container containing the formulation for nasal administration.

TABLE 2

Examples of formulations for nasal administration

| Ingredient | Function | Amount (% w/w) |
|---|---|---|
| Example for a liquid formulation comprising a corticosteroid | | |
| Fluticasone Propionate Micronised | Active | 0.05 |
| Dextrose Anhydrous | Osmolarity agent | 5 |
| Phenylethyl Alcohol USP | Preservative | 0.25 |
| Avicel RC591 (GI) | Suspending agent | 1.50 |
| Benzalkonium Chloride EP/USNF/JP | Preservative | 0.02 |
| Polysorbate 80 (GI) | Wetting agent | 0.005 |
| Purified Water | Vehicle | Ad 100.0 |
| Example for a liquid formulation comprising a vasoconstrictor | | |
| Xylometazoline Hydrochloride | Active Ingredient | 0.1 |
| Sodium dihydrogen phosphate dihydrate | Buffering Agent | 0.28 |
| Disodium phosphate dodecahydrate | Buffering Agent | 0.3 |
| Disodium edetate | Chelating agent | 0.05 |
| Benzalkonium Chloride | Preservative | 0.01 |
| Sodium Chloride | Isotonicity regulator | 0.7 |
| Purified water | Vehicle | Ad 100 |
| Example for a liquid formulation comprising a vasoconstrictor and a moisturizing agent | | |
| Oxymetazoline Hydrochloride | Active Ingredient | 0.05 |
| Sodium dihydrogen phosphate dihydrate | Buffering Agent | 0.2 |
| Disodium phosphate dodecahydrate | Buffering Agent | 0.28 |
| Disodium edetate | Chelating agent | 0.05 |
| Benzalkonium Chloride | Preservative | 0.01 |
| Sorbitol 70% (non-crystallising) | Moisturizing Agent | 1.4 |
| Sodium Chloride | Isotonicity regulator | 0.5 |
| Levomenthol | Aroma | 0.03 |
| Cineol | Aroma | 0.02 |
| Castor oil, polyoxyl hydrogenated | Solubiliser | 0.275 |
| Purified water | Vehicle | ad 100 |

The invention claimed is:

1. A combination product comprising a dispensing head (10, 10') mounted on a top of a container (20, 20') containing a formulation for nasal administration, and a solidified skin care balm (50) for application around the nose contained in a balm holder element (30, 30") located on a bottom (24) of the container (20).

2. A combination product according to claim 1 wherein the dispensing head (10, 10') is a metered dose spray pump.

3. A combination product according to claim 1, wherein the balm holder element (30, 30") comprises a base element (34, 34', 34") on which the balm (50) is mounted, and a balm cover (32, 32") with a cylindrical portion (33, 33") surrounding the balm (50), and a cover portion (36, 36").

4. A combination product according to claim 3, wherein the cylindrical portion (33, 33") of the balm cover (32, 32") is aligned with a cylindrical wall (22, 22') of the container (20, 20') containing the formulation.

5. A combination product according to claim 3, wherein the balm cover (32) is attached to the bottom (24) of the container.

6. A combination product according to claim 5, wherein the balm cover (32) is glued to the bottom (24) of the container (20, 20').

7. A combination product according to claim 3, wherein the cover portion (36) is dome-shaped and matches a recess in the bottom (24) of the container (20) containing the formulation.

8. A combination product according to claim 3, wherein the balm cover is clipped or snap-fitted to the bottom (24) of the container.

9. A combination product according to claim 1, wherein the base element (34") is attached to the bottom (24) of the container (20').

10. A combination product according to claim 1, wherein the liquid formulation comprises a saline solution and/or an active ingredient selected from the group of vasoconstrictors, antiallergic agents and corticosteroids.

11. A combination product according to claim 10, wherein the active ingredient is xylometazoline or a pharmaceutically acceptable salt thereof.

12. A combination product according to claim 1, wherein the balm comprises an active ingredient having skin soothing properties, in particular selected from the group comprising ectoin, dexpanthenol, aloe vera, calendula, bisabolol and niacinamide.

13. A combination product according to claim 1, wherein the solidified balm (50) has substantially a hemispherical shape.

14. A combination product according to claim 1, wherein the balm comprises one or several skin conditioning agents.

15. A combination product according to claim 1, wherein the balm (50) comprises an active ingredient that is a botanical extract.

16. A balm holder element (30, 30") comprising: a base element (34, 34', 34") on which a balm (50) is mounted, a balm cover (32, 32") with a cylindrical portion (33, 33") surrounding the balm (50), and a cover portion (36, 36"), wherein the balm holder element (30, 30' ') is attachable to a nasal spray dispenser.

17. A method for treating nasal discomfort whereby a cooling and soothing effect is provided to a perinasal skin area, comprising the step of using the combination product according to claim 1 by applying the balm (50) to the perinasal skin area and administering the formulation for nasal administration into a nostril.

18. A method for treating runny nose whereby irritated skin is soothed, comprising the step of using the combination product according to claim 1 by applying the balm (50) to an irritated perinasal skin area and administering the formulation for nasal administration into a nostril.

* * * * *